United States Patent [19]
Waylett, Jr.

[11] Patent Number: 5,465,629
[45] Date of Patent: Nov. 14, 1995

[54] LIQUID DISPENSING SYSTEM WITH ACOUSTIC SENSING MEANS

[75] Inventor: John E. Waylett, Jr., Marshfield, Mass.

[73] Assignee: Behring Diagnostics Inc., Westwood, Mass.

[21] Appl. No.: 225,494

[22] Filed: Apr. 11, 1994

Related U.S. Application Data

[63] Continuation of Ser. No. 894,863, Jun. 8, 1992, abandoned.

[51] Int. Cl.⁶ ..................................................... B01L 3/02
[52] U.S. Cl. .................................. 73/864.24; 73/864.16
[58] Field of Search .......................... 73/863.01, 864.23, 73/864.24, 864.25, 290 V, 589, 864.13, 864.16, 864.18; 422/100; 340/618, 621; 367/908

[56] References Cited

U.S. PATENT DOCUMENTS

| 2,808,581 | 12/1954 | Findlay . | |
|---|---|---|---|
| 3,237,451 | 3/1966 | Haeff . | |
| 3,474,902 | 9/1968 | Putman . | |
| 3,635,094 | 1/1972 | Oberli | 73/423 A |
| 3,754,444 | 8/1973 | Ure et al. | 73/423 A |
| 3,759,667 | 9/1973 | Bannister et al. | 23/259 |
| 3,825,025 | 7/1974 | Samuel et al. . | |
| 3,834,233 | 9/1974 | Willis et al. . | |
| 3,894,438 | 7/1975 | Ginsberg | 73/423 A |
| 3,992,158 | 11/1976 | Przybylowicz et al. . | |
| 4,041,995 | 8/1977 | Columbus . | |
| 4,053,381 | 10/1977 | Hamblen et al. . | |
| 4,175,441 | 11/1979 | Urbanek et al. . | |
| 4,189,722 | 2/1980 | Lerner . | |
| 4,228,831 | 10/1980 | Kerns . | |
| 4,258,001 | 3/1981 | Pierce et al. . | |

(List continued on next page.)

FOREIGN PATENT DOCUMENTS

| 0169071 | 1/1986 | European Pat. Off. . |
|---|---|---|
| 0273128 | 10/1986 | European Pat. Off. . |
| 0199466 | 10/1986 | European Pat. Off. . |
| 0209872 | 1/1987 | European Pat. Off. . |
| 0210014 | 1/1987 | European Pat. Off. . |
| 0223751 | 5/1987 | European Pat. Off. . |
| 0488761 | 6/1992 | European Pat. Off. . |
| 2241080 | 3/1975 | France . |
| 3039475 | 5/1980 | Germany . |
| 3737204 | 5/1989 | Germany . |
| 56-164957 | 12/1981 | Japan . |
| 56-164958 | 12/1981 | Japan . |
| 59-052759 | 3/1984 | Japan . |
| 59-164916 | 9/1984 | Japan . |
| 61-137067 | 6/1986 | Japan . |
| 63-019520 | 1/1988 | Japan . |
| 63-075565 | 4/1988 | Japan . |
| 63-109330 | 5/1988 | Japan . |
| 63-109373 | 5/1988 | Japan . |
| 63-108231 | 5/1988 | Japan . |
| 63-100330 | 5/1988 | Japan . |
| 550998 | 4/1973 | Switzerland . |
| 777450 | 11/1980 | U.S.S.R. . |
| 663946 | 1/1952 | United Kingdom . |
| 1104619 | 2/1968 | United Kingdom . |
| 2144550 | 4/1985 | United Kingdom . |
| 2177510 | 1/1987 | United Kingdom . |
| WO86/03834 | 7/1986 | WIPO . |
| 88/08985 | 11/1988 | WIPO . |

Primary Examiner—Hezron E. Williams
Assistant Examiner—Nashmiya Ashraf
Attorney, Agent, or Firm—Curtis, Morris & Safford

[57] ABSTRACT

There is described a liquid dispensing system for the transfer of liquids from one location to another. The liquid dispensing system includes a pipette in combination with a sound source and a sound detector. The liquid dispensing system can be used in combination with an automated clinical analyzer and can be utilized to provide one or more of a number of functions including sensing the proximity of a pipette tip to a surface, determining the depth to which a pipette tip has penetrated into a volume of liquid, determining whether a pipette tip has been affixed to a pipette stem and determining the amount of liquid aspirated into a pipette tip.

18 Claims, 6 Drawing Sheets

U.S. PATENT DOCUMENTS

| | | |
|---|---|---|
| 4,287,155 | 9/1981 | Tersteeg et al. . |
| 4,320,659 | 3/1982 | Lynnworth et al. . |
| 4,326,851 | 4/1982 | Bello et al. .................. 23/230 R |
| 4,340,390 | 7/1982 | Collins et al. . |
| 4,341,736 | 7/1982 | Drbal et al. . |
| 4,474,061 | 10/1984 | Parker . |
| 4,478,094 | 10/1984 | Saloman et al. . |
| 4,599,892 | 7/1986 | Doshi . |
| 4,675,301 | 6/1987 | Charneski et al. . |
| 4,704,902 | 11/1987 | Doshi . |
| 4,715,413 | 12/1987 | Backlund et al. . |
| 4,736,638 | 4/1988 | Okawa et al. ................. 73/864.24 |
| 4,777,832 | 10/1988 | Prodosmo et al. . |
| 4,790,183 | 12/1988 | Pfost et al. . |
| 4,794,085 | 12/1988 | Jessop et al. ..................... 436/54 |
| 4,818,492 | 4/1989 | Shimizu ............................ 422/100 |
| 4,846,003 | 7/1989 | Marquiss .......................... 73/864.24 |
| 4,864,856 | 9/1989 | Ichikawa et al. . |
| 4,893,515 | 1/1990 | Uchida . |
| 4,912,976 | 4/1990 | Labriola, II ..................... 73/290 R |
| 5,045,286 | 9/1991 | Kitajima et al. ................. 422/100 |
| 5,083,470 | 1/1992 | Davis et al. ..................... 73/864.24 |

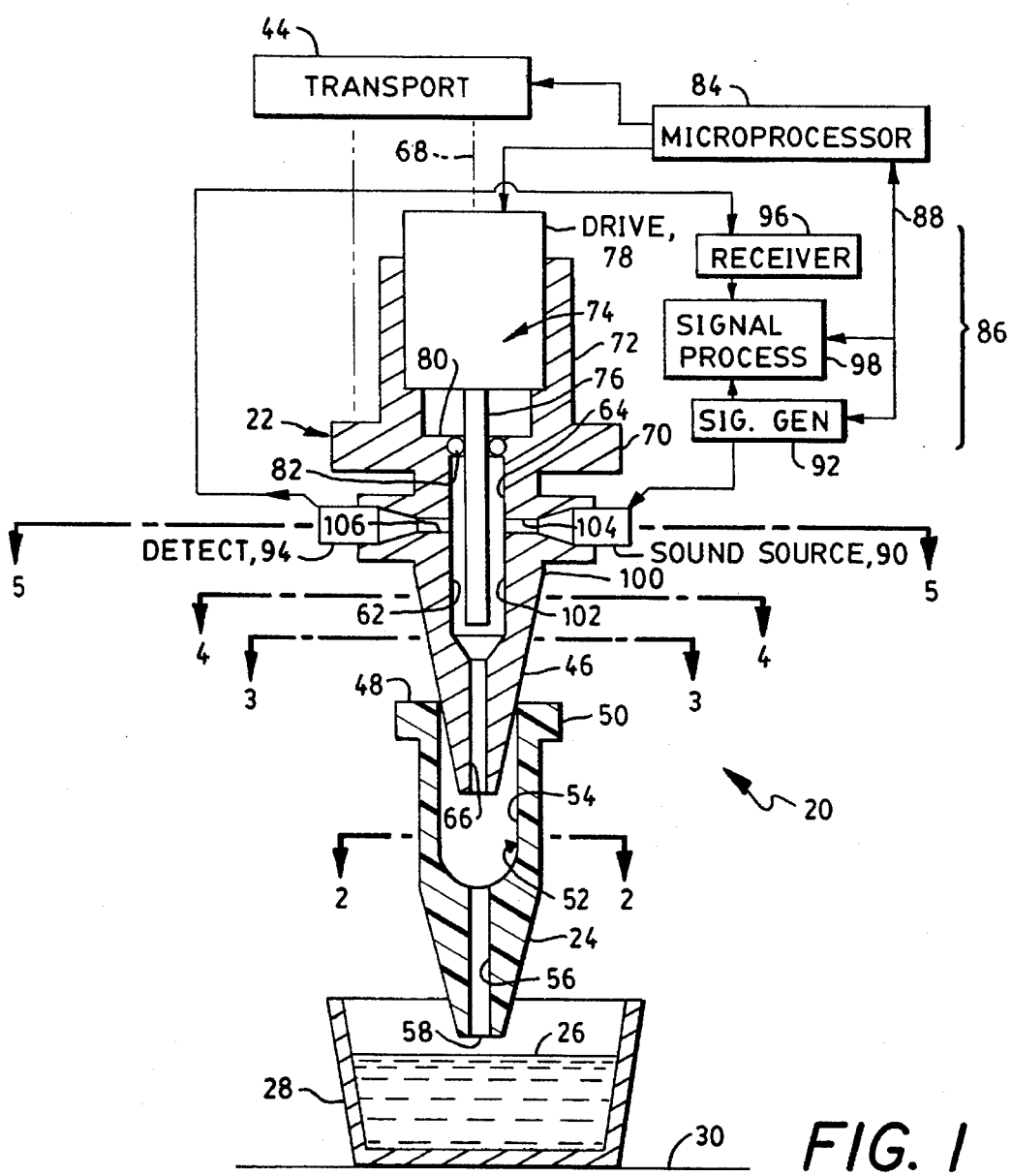
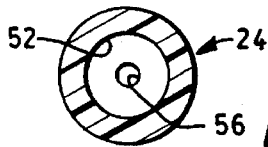
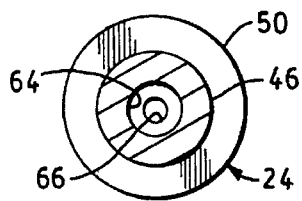
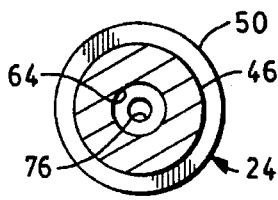
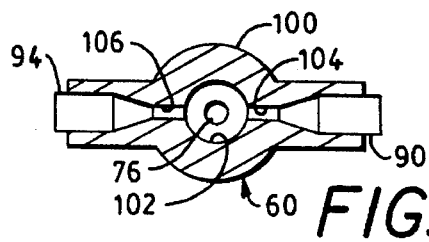

LIQUID DISPENSING SYSTEM WITH ACOUSTIC SENSING MEANS

This application is a continuation of application Ser. No. 07/894,863, filed Jun. 8, 1992, now abandoned.

BACKGROUND OF THE INVENTION

This invention relates generally to a liquid dispensing system for use in clinical analyzers. More particularly the invention relates to a liquid dispensing system which includes acoustic sensing means.

Pipettes are employed in automated analyzers for transporting liquids between reservoirs which hold liquid samples and/or reagents and for transporting liquids from such reservoirs to test sites such as in assay cartridges to conduct various tests. The pipette is typically carried by a transport mechanism which provides for both horizontal and vertical movement so as to enable the pipette tip to be lowered into a liquid in a reservoir for aspiration of the liquid, and for transporting the liquid to a test site whereat the pipette is lowered to an optimal position for dispensing the liquid. Some type of device, such as a piston assembly, which may be incorporated into the pipette, is operated electronically to aspirate liquid into the pipette and to dispense liquid from the pipette.

Various types of chemical tests can be performed by such automated test equipment, an example of testing of considerable interest being the assay of biological substances for human health care. Automated test equipment allows large numbers of test samples to be processed rapidly. Such equipment is employed in health care institutions including hospitals and laboratories. Biological fluids, such as whole blood, plasma or serum are tested to find evidence of disease, to monitor therapeutic drug levels, etc. In such automated analyzers disposable pipette tips are typically used for the delivery of one liquid only and then discarded so as to avoid contamination which could lead to errors in the assay result.

It is desirable, when aspirating liquid into the pipette tip, to lower the orifice of the pipette tip into the liquid to a controlled distance which is sufficient for the aspiration of the desired amount of liquid. Inaccurate positioning of the pipette tip relative to the surface of the liquid may introduce an error in the amount of liquid aspirated into the tip. Further, lowering the tip into the liquid to an excessive distance increases the possibility that a small amount of liquid may adhere to the outside wall of the pipette tip when the tip is withdrawn from the liquid. Liquid adhering to the outer wall of the pipette tip could result in an inaccurate amount of fluid being dispensed.

The use of disposable pipette tips presents a problem in controlling the depth to which the pipette tip is lowered into a liquid. The disposable pipette tips, which are typically made of a polymeric material, are provided in a storage tray within the instrument. Initially the pipette, which typically has a metal stem, is advanced downwardly to secure a disposable tip by frictional contact. Since the polymeric materials from which the tips are made are flexible there may be some variation from tip to tip as to the distance of the tip orifice from the metal pipette stem. Thus, any variation in the positioning of the tip on the pipette stem can result in an error in the desired positioning of the pipette tip in the liquid during the aspiration step.

In addition to the above mentioned consideration it is preferable that such automated analyzers, the operation of which is typically controlled by a software program embedded in a microprocessor, be able to recognize whether a disposable pipette tip has in fact been properly attached to the pipette stem during the dispense cycle. Further, it would be advantageous for the analyzers to have the capability to determine the level of liquid aspirated into the pipette tip.

The prior art liquid dispensing devices are not satisfactory in all instances. For example, devices which are capable of sensing the liquid level during the aspiration step may not be able to determine the amount of liquid which is aspirated into the pipette tip. Accordingly, as the state of the art advances and more demands are made on the instrument systems there is a continuing need for novel liquid dispense systems.

BRIEF SUMMARY OF THE INVENTION

It is therefore an object of this invention to provide a novel liquid dispense system.

Another object is to provide a liquid dispensing system which is capable of sensing the proximity of a pipette tip to a surface.

A further object is to provide a liquid dispensing system which can determine the depth to which a pipette tip has penetrated into a volume of liquid.

Still another object is to provide a liquid dispensing system which can determine whether a pipette tip is affixed to a pipette stem.

Yet another object is to provide a liquid dispensing system which has the capability of determining the amount of liquid which has been aspirated into a pipette tip.

SUMMARY OF THE INVENTION

These and other object and advantages are accomplished in accordance with the invention by providing a liquid dispensing system which includes a sound source and a sound detector in combination with a pipette.

The pipette includes a pipette tip holder which is adapted to carry a pipette tip. In a preferred embodiment the pipette tip holder has a conically narrowing nose for insertion within a disposable tip to make frictional contact with a proximal lip of the tip, so as to hold the tip securely during the transfer of liquid from one location to another. The pipette tip has a central cavity terminating in a distal orifice through which liquid is aspirated into the cavity, and through which liquid is dispensed therefrom. The holder has a central chamber which opens into the tip cavity upon engagement of the holder with the tip. The pipette further comprises a piston assembly connecting with the holder on a top side thereof, opposite the tip. A piston in the piston assembly extends into the holder chamber. The piston assembly includes a drive mechanism such as a stepping motor for retracting and for advancing the piston within the chamber to create vacuum (negative) pressure for aspirating liquid into the tip cavity, and positive pressure for dispensing liquid from the tip cavity.

The holder chamber is defined by a wall which encircles the chamber and provides the chamber with a substantially cylindrical shape in a preferred embodiment of the invention. The piston has a circular cylindrical shape. There is an annular space between the piston and the holder wall. In a preferred embodiment of the liquid dispensing system of the invention, the sound source is a miniature speaker operated by a speaker coil. The speaker can be affixed to the holder wall and a sound conduit can be arranged to pass from the speaker through the holder wall to open into the annular space of the holder chamber. The sound detector can be a microphone which can be affixed to the holder wall, and open into the annular space of the holder chamber, preferably at a location diametrically opposite the speaker. The liquid dispensing system further comprises a signal processor which connects with the sound source and the detector to analyze a sonic signal received at the detector. The received sonic signal, based on parameters such as its intensity and phase, can be analyzed to provide information relating to the location of a surface, such as the surface of a volume of liquid in a container or a reservoir or the surface of an assay element, relative to the distal end of the tip. In addition, in the case of an instrument which utilizes disposable pipette tips, the analysis of the received sonic signal can provide information relating to the presence or absence of a pipette tip on the pipette tip holder. The received sonic signal can also provide information concerning the amount of liquid which has been aspirated into the pipette tip.

It has been found, in accordance with the invention, that the parameters of the received sonic signal are dependent on: (1) the frequency of the sound; (2) on the geometry of the tip cavity as well as the geometry, or configuration, of the holder chamber including the annular space thereof; (3) on the position of the sound source, e.g., a transducer, and the sound detector relative to the pipette tip cavity; and most significantly (4) on the surface being approached relative to the orifice at the distal end of the pipette tip. In a typical pipette, the overall length of the internal space, from the orifice of the tip, through the tip cavity and the holder chamber, to the top of the annular space surrounding the piston, can be from approximately two to three inches. The internal space has a diameter which varies along a central axis of the pipette, but typically is less than approximately one-eighth inch.

The liquid dispensing system of the invention may be operated at any suitable frequency within the audible range, e.g., from about 50 to about 5000 Hertz (Hz). At relatively low frequencies, such as 50 Hz wherein the sound wavelength is much greater than the dimensions of the internal space, the signature of the received sound is substantially free of any resonances within the pipette, except for the possible presence of harmonics of the sound which may be affected by resonances due to the shape of the internal space. Alternatively, when the liquid dispensing system is operated at relatively high frequency such as 5000 Hz wherein the sound wavelength is smaller than the dimensions of the internal space, the signature of the received sound is dependent on the shape of the internal space.

As is well known, the signature of a sonic signal includes all aspects of the signal waveform, including an amplitude pattern of the waveform, as well as a phase pattern and frequency components of the waveform. The signature has been found to vary in a characteristic fashion as the pipette tip, initially distant from a surface, approaches that surface and further, in some cases, when the orifice of the pipette tip is closed such as when the tip enters a liquid. The signature varies still further when liquid is aspirated into the tip cavity, due to a change in the shape of the internal space as the piston is withdrawn and liquid fills the bottom of the cavity. The liquid dispensing system may be operated with a controller device such as a microprocessor which stores signature data at different frequencies to enable identification of the location of a surface relative to the tip orifice by recognition of the sound signature. If desired, low frequency sound may be employed for sounding the cavity upon approach of the pipette to the surface, and high frequency sound may be employed for measuring the liquid level within the cavity during aspiration and dispensing of a liquid, as well as during a transportation of the liquid by the pipette tip between two locations, e.g., a reservoir and a test site.

In the preferred embodiment of the invention wherein the liquid dispensing system is utilized to determine when the pipette tip has penetrated the surface of a volume of liquid, the amplitude of the received sonic signal is dependent upon the frequency of the sound emitted by the source; that is to say, the received sonic signal may undergo a sudden rise or drop in intensity as the tip approaches and contacts the liquid surface. At relatively low frequencies, e.g., from about 50 to about 500 Hz, the received sonic signal undergoes a sudden change in intensity as the tip approaches and contacts the liquid. The sudden change in sound intensity is due to the closure of the tip orifice which prevents radiation of sonic energy out of the orifice, thereby increasing the reflected intensity of the sound from the orifice of the tip. The reflected sound interacts with the other sources picked up within the cavity which are out of phase.

At frequencies within the range of from about 400 to about 600 Hz the intensity of the received sonic signal decreases due to cancellation with other sources sensed within the cavity which are out of phase while at frequencies in the range of from about 1500 Hz to about 2000 Hz the intensity increases due to resonance in the cavity. The phase—amplitude signatures for frequencies within the range of from about 2000 Hz to about 5000 Hz are dependent upon the internal geometry of the pipette device, excluding the pipette tip.

In a preferred embodiment of the invention a low frequency sound signal, i.e., in the range of from about 400 Hz to about 600 Hz, is utilized as the pipette tip approaches a liquid surface. A control signal is outputted from the controller to the pipette transport device to terminate the downward movement of the pipette as the pipette tip comes into contact with and enters the liquid. High frequency sound, i.e., in the range of from about 1500 Hz to about 2000 Hz, is then employed as the liquid is aspirated into the pipette tip and subsequently when the pipette tip is retracted from the liquid and the pipette is transported to another location.

The liquid dispensing system of the invention is also capable of determining whether a pipette tip is affixed to the pipette such as where a disposable pipette tip is picked up by the pipette at the beginning of a liquid dispense cycle. The amplitude of the signal changes when the tip is affixed to the holder. In addition, the liquid dispensing system can be utilized to calibrate the pipette position.

BRIEF DESCRIPTION OF THE DRAWINGS

For a better understanding of the invention as well as other objects and further features thereof, reference is made to the following detailed description of various preferred embodiments thereof, taken in connection with the accompanying drawings wherein:

FIG. 1 is a longitudinal sectional view of a pipette with connection to components of a liquid dispensing apparatus, portions of the figure being shown diagrammatically;

FIGS. 2, 3, 4, and 5 are cross-sectional views of the pipette taken along the lines 2—2, 3—3, 4—4, and 5—5, respectively, in FIG. 1;

DETAILED DESCRIPTION OF THE PREFERRED EMBODIMENTS

Figure 6:
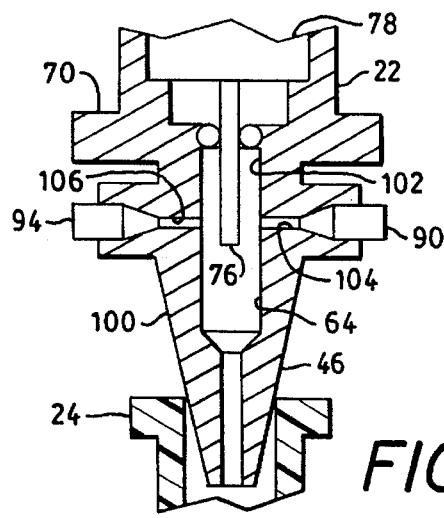
FIG. 6 is a fragmentary portion of the pipette of FIG. 1 showing a piston in a retracted position after aspiration of liquid, as compared to an extended position of the piston depicted in FIG. 1.

Referring now to FIGS. 1–6 there is illustrated a liquid dispensing system 20 according to the invention which includes a pipette 22. As illustrated the pipette 22 has affixed thereto a replaceable pipette tip 24 for aspirating and dispensing liquid such as a sample liquid 26 stored in reservoir 28 which is supported on a platform 30. Although one such sample liquid 26 is shown for the purpose of describing the liquid dispensing system 20, it will be apparent to those skilled in the art that any number of sample liquid reservoirs can be present in an automated clinical analyzer. The liquid dispensing system 20 will be described in the context of its use in an automated clinical analyzer (not shown). Such automated clinical analyzers are well known in the art and those skilled in the art will know with certainty the functions of the elements of the analyzers to which reference is made.

In such automated clinical analyzers a plurality of assay elements is typically carried by a conveyor in a temperature controlled chamber, or incubator, for maintaining the assay elements at the desired temperature at which the assay(s) of the sample liquid must be carried out. The assay elements may be all of the same type, that is all may be specific for the same component of sample liquids, or they may be of different types which are specific for different components of sample liquids.

The liquid dispensing system 20 includes a transport device 44, indicated diagrammatically, which may be of any suitable type. The transport device 44 is capable of moving the pipette 22 laterally (the X-direction), vertically (the Z-direction) and from front to back (the Y-direction) in the instrument to enable the pipette to pick up a pipette tip (where disposable tips are used), aspirate liquid into the pipette tip from a sample liquid reservoir and to dispense a desired amount of sample liquid to an assay element. As is known in the art the sample fluid may be dispensed to the assay element prior to, or after, the assay element is inserted into the temperature-controlled chamber.

As shown, the pipette 22 preferably includes a tapered stem 46 which makes frictional contact with a proximal lip 48 of the tip 24 to affix the tip 24 securely to the stem and to seal the stem 46 and tip 24 together. A flange assembly 50 at the proximal end of the tip 24 permits engagement of the tip 24 with a device (not shown) for removing the tip 24 from the pipette stem 46, and also facilitates storage of the tip 24, prior to its use, in a pipette tip holder (not shown).

The tip 24 has a cavity 52 for holding liquid, such as the liquid 26 upon aspiration of the liquid 26 into the tip 24. As shown cavity 52 comprises a cylindrical section 54 of relatively large diameter and a narrow tubular passage 56 extending from a bottom of the cylindrical section 54 to an orifice 58 at the distal end of the tip 24. A lower portion of the pipette 22, which may be referred to as a pipette tip holder, includes the stem 46 and a central chamber 62. The chamber 62 comprises an upper cylindrical portion 64 and a lower tubular portion 66 which communicates between the upper cylindrical portion 64 and the tip cavity 52 upon engagement of the stem 46 with the tip 24. The upper cylindrical portion 64 and the lower tubular portion 66 of the chamber 62 are disposed coaxially about a central longitudinal axis 68 of the pipette 22. Upon engagement of the stem 46 with the tip 24, the cylindrical section 54 and the tubular passage 56 of the cavity 52 are also disposed coaxially along the axis 68.

The pipette 22 further comprises a flange assembly 70 by which the transport 44 connects with the pipette 22. The top of the stem 46 connects with the bottom side of the flange assembly 70. Above the flange assembly 70, there extends a frame 72 of the pipette 22 for holding a piston unit 74 which includes a piston 76 and a drive 78 for advancing the piston 76 downwardly along the axis 68 towards the tip 24, and for retracting the piston 76 upwardly along the axis 68 away from the tip 24. The piston 76 enters the central chamber 62 via an opening in a top wall 80 of the chamber 62, the opening in the top wall 80 being formed with the aid of an O-ring 82 which provides for an air-tight seal for the passage of the piston 76 through the top wall 80. An upward movement of the piston 76 tends to increase the volume of the chamber 62, thereby to create vacuum or negative air pressure, within the chamber 62, which draws air from the tip cavity 52 into the holder chamber 62 for aspirating liquid, such as the liquid 26, into the cavity 52. Advancing the piston 76 into the holder chamber 62 decreases the volume of the chamber 62, thereby to provide a positive air pressure which pushes air out of the chamber 62 into the tip cavity 52 for expelling and dispensing liquid from the tip 24 via the tip orifice 58. Thus, the piston unit 74 provides for aspiration of liquid into, and dispensing of liquid from, the tip 24. The piston drive 78 includes a stepping motor (not shown) activated by electrical signals from a microprocessor 84 which in a preferred embodiment is used to control the operation of the liquid dispense system 20 as well as the overall clinical analyzer. The microprocessor 84 also provides drive signals to the transport 44 to control the movement of the pipette 22 as well as the aspiration into, and dispensing of liquid from, the pipette tip 24.

In accordance with the invention, the liquid dispense system 20 further comprises acoustic apparatus 86 operatively connecting with the pipette 22. Although it has been stated previously herein that the liquid dispense system of the invention can be utilized to provide various types of information including whether a disposable pipette tip 24 has been affixed to the stem 46 of the pipette 22 and how much liquid has been aspirated into the tip 24, the liquid dispense system 20 will first be described with respect to the embodiment wherein it is exploited to sense the position of the level of the liquid 26 in the reservoir 28 relative to the orifice 58. In the process of aspirating liquid 26 into the pipette tip 24, the pipette 22 is first positioned above the reservoir 28 by the transport 44, and is then lowered to bring the distal end of the tip 24, specifically the orifice 58, into contact with the liquid 26. Thereupon, the piston unit 74 is operated to retract the piston 76 from the holder chamber 62 for aspiration of the liquid 26 into the tubular passage 56. Further aspiration raises the liquid 26 sufficiently to bring it into the bottom of the cylindrical section 54 of the tip cavity 52. The amount of retraction of the piston 76 is predesignated by the microprocessor 84 to transfer a specific volume of the liquid 26 from the reservoir 28 into the pipette tip 24. It will be apparent to those skilled in the art that the volume of liquid aspirated into the tip may be that which is required for a single assay in which case substantially the entire volume is dispensed to one assay element. Alternatively, sufficient liquid for a plurality of assays maybe aspirated into the tip and portions of the liquid dispensed to each of a plurality of assay elements.

To facilitate the process of moving the pipette tip 24 to contact the top surface of the liquid 26, so as to initiate aspiration of the liquid 26 through the orifice 58, the acoustic apparatus 86 outputs a signal on line 88 to signal the microprocessor that the orifice 58 has been closed by contact with the top surface of the liquid 26. This signal indicates that the pipette 22 has been lowered sufficiently to make the desired contact between the tip 24 and the liquid 26. The microprocessor 84 responds by terminating advancement of the pipette 22. The signal provided to the microprocessor 84 by the acoustic apparatus 86 greatly increases the accuracy in the positioning of the pipette tip 24 relative to the top surface of the liquid 26, and thereby concomitantly decreases the possibility of introducing error into the volume of liquid to be dispensed.

Subsequently, the transport device 44 operates to raise the pipette 22 a distance sufficient to allow the pipette tip to clear the top of reservoir 28 and the pipette is transported laterally to a position above an assay element. The pipette is then driven downwardly to a desired dispense position above the assay element and the desired volume of sample liquid is dispensed to the assay element. In dispensing relatively small volumes of liquid, e.g., from about 10 μl to about 100 μl, it is known in the art that the orifice of the pipette tip must be positioned at a precisely controlled distance above the assay element. The positioning of the pipette at the desired dispense position can be carried out in accordance of the liquid dispense system of the invention.

The acoustic apparatus 86 comprises a sound generator device 87 (FIG. 7) which includes a sound source 90 and a signal generator 92; a sound detecting device 93 which includes a sound detector 94 (FIG. 7) and a receiver 96, e.g., an amplifier or a buffer; and a signal processor 98. The pipette stem 46 includes a wall 100 which encircles the central chamber 62. The sound source 90 and the sound detector 94 are mounted to the wall 100 of the stem 46 and, in a preferred embodiment of the invention, are positioned diametrically opposite each other. The sound source 90 may comprise a speaker coil and a movable diaphragm (not shown) set into vibration by the speaker coil in response to an electric activating signal provided by the signal generator 92. The sound detector 94 may comprise a microphone. The wall 100 has a circular cylindrical inner surface disposed symmetrically about the axis 68 and, in cooperation with the centrally disposed piston 76, defines an annular space 102 which encircles the piston 76, the annular space 102 being a part of the central chamber 62. A conduit 104 passes through the wall 100 to provide sonic communication between the source 90 and the annular space 102. A conduit 106 passes through the wall 100 to provide for sonic communication between the detector 94 and the annular space 102.

The signal processor 98, is operative in a manner to be described, to receive the state counter information from the sound source 90. The detector 94 detects sound waves within the annular space 102 resulting from the energization of the source 90, and converts a sonic signal carried by the sound waves to an electric signal which is applied to the receiver 96. Upon reception of the electric signal from the detector 94, the receiver 96 outputs a received signal to the signal processor 98. The processor 98, in a manner to be described, analyzes the received signal to output the aforementioned signal on line 88 indicating contact of the tip orifice 58 with the surface of the liquid 26 in reservoir 28.

It is noted that the configuration of the annular space 102 can vary from a relatively long annular space, as depicted in FIG. 1 for an advanced position of the piston 76, to a relatively short annular space, as depicted in FIG. 6 for a retracted position of the piston 76. The nature of the sound waves detected at the detector 94, including a signature of the sonic signal carried by the sound waves, is dependent on the configuration of both the central chamber 62 of the stem 46 and the configuration of the cavity 52 of the tip 24 because of the acoustic coupling between the chamber 62 and the cavity 52 via the tubular portion 66 of the chamber 62. The configuration of the cavity 62 of the pipette stem 46 with respect to available air space suitable for reflecting and/or resonating sonic waves is dependent on the level of a liquid which is aspirated into the cavity 52 of the tip 24. Thus, in response to a known position of the piston 76, there is a recognizable signature to a received sonic signal representative of the position of a liquid level relative to the orifice 58 both above and below the orifice 58.

Figure 7:
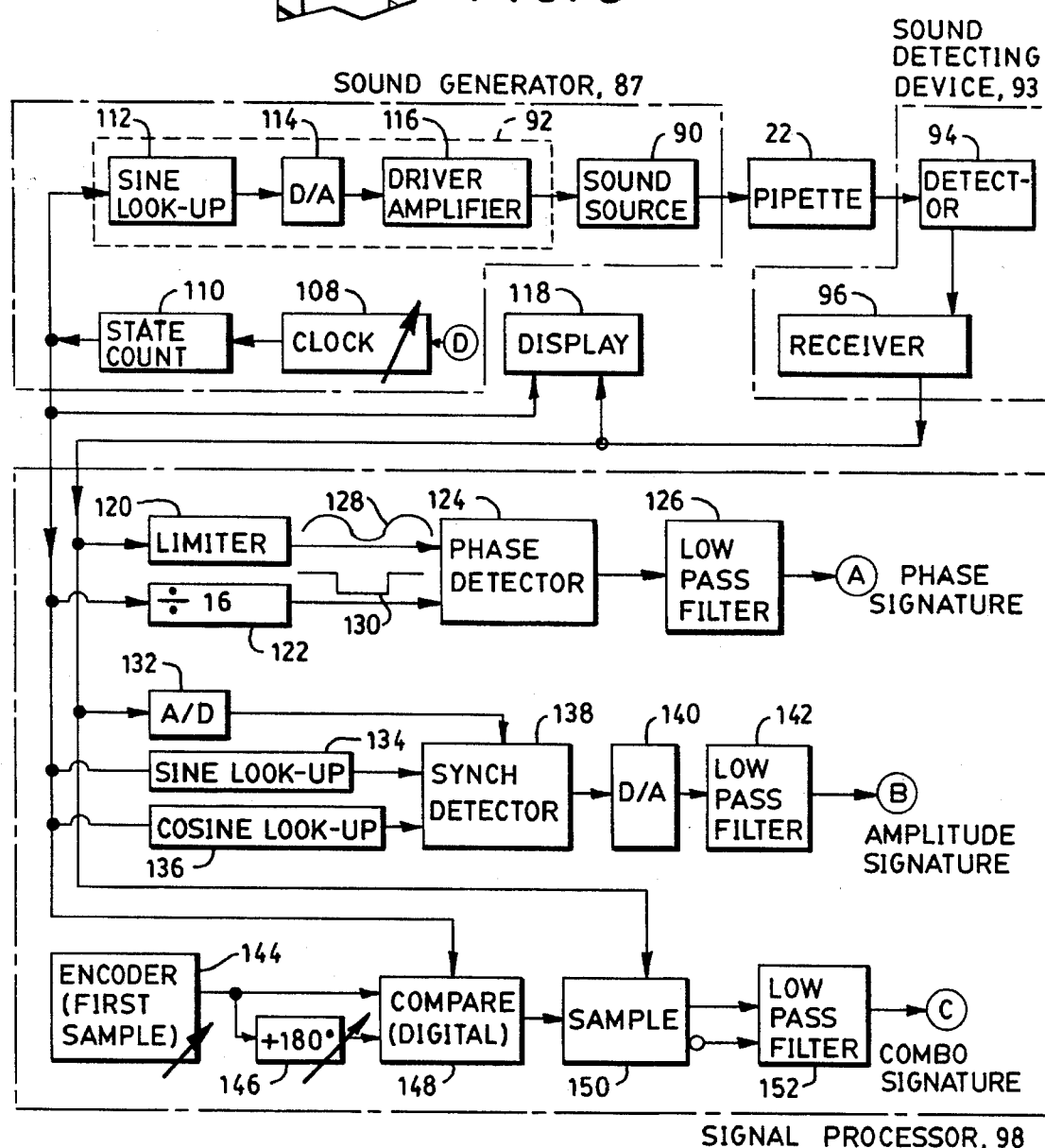
FIG. 7 is a block diagram of electrical circuitry employed in the liquid dispensing apparatus of FIG. 1.

FIG. 7 shows details in the construction of circuitry of the signal processor 98 and of the signal generator 92. The circuitry of FIG. 7 provides for the generation of the sonic signal within the pipette 22 (FIG. 1), and for the evaluation of the sonic signal to determine the proximity of the level of the liquid 26 in the reservoir 28 to the tip orifice 58. This is accomplished by recognition of a change in signal amplitude and/or phase to develop a signature which provides data on the proximity of the liquid level to the tip orifice.

In a preferred embodiment of the invention, the signal generator 92 comprises a microprocessor-programmable, controlled clock 108, a state counter 110 a sine look-up table 112, a digital to analog converter 114 and a drive amplifier 116. The clock 108 drives the state counter 110 and the state of the counter 110 is passed to the sine look-up table 112 the output from which goes to digital-to-analog converter 114. The output from converter 114 is buffered by the drive amplifier 116. The state counter 110, in combination with the look-up table 112 and the converter 114, provides a stepwise approximation to a sinusoidal waveform for energizing the sound source 90. By way of example, the state counter 110 may count modulo-32 wherein there are 32 counts per cycle of the sinusoidal waveform. This corresponds to 11.25 degrees of phase per count. The look-up table 112 provides the value of amplitude of the sinusoidal waveform corresponding to each count. The values are outputted as digital values to the converter 114 to be converted to analog signal values. The analog signal values are amplified by the amplifier 116 and smoothed by filtering (not shown) within the amplifier 116 to present a substantially sinusoidal signal to the sound source 90. The amplifier 116 provides sufficient power to the signal for driving the source 90.

The frequency of the sonic signal produced by the source 90 is determined by the repetition frequency of pulses applied by the programmable clock 108 to the counter 110. In the example presented in FIG. 7, wherein there are 32 counts per cycle of the sonic signal, the repetition frequency of the clock 108 is 32 times greater than the frequency of the sonic signal. Additional smoothing of the step-wise approximation to the sinusoid is provided by the response of the speaker within the source 90. The receiver 96 includes an amplifier and a band-pass filter (not shown) for amplifying and filtering the signal outputted by the detector 94. In the event that it is desired to operate the clock 108 at differing frequencies during different phases of measurement of the liquid level, then the passband of the receiver 96 is adequately broad to accommodate the range of frequencies of the received signal. Alternatively, if desired, electronic tuning of the receiver 96 may be employed. A desired operating frequency of the clock 108 may be designated at terminal D by a signal applied thereto from the microprocessor 84 (FIG. 1 ). The liquid dispense system may include a display 118 for viewing a signal outputted by the receiver 96. Preferably, the display 118 is synchronized with the output signal of the counter 110 so as to enable the presentation of phase shift, or time delay, in the received sonic signal, as measured relative to the time of generation of the sonic signal. It will be appreciated by those skilled in the art that such synchronization may be controlled by microprocessor 84.

Figure 11:
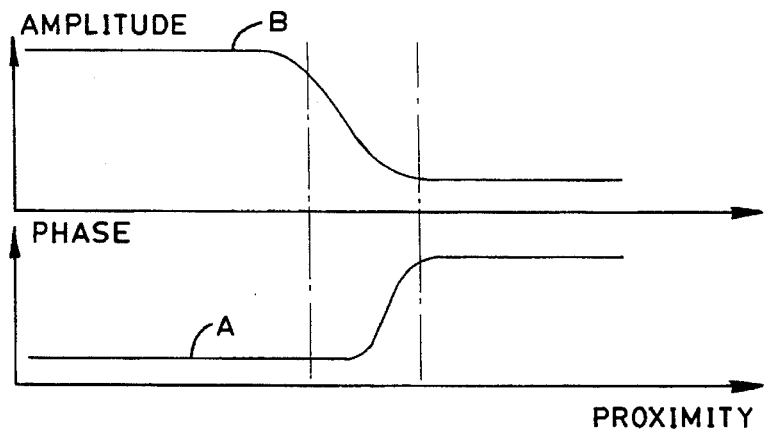
FIG. 11 is an illustrative signature change (both for amplitude and phase) of the signal vs proximity to a surface.

The signal processor 98 has the capacity to measure the phase angle of the received sonic signal relative to the phase angle of the transmitted sonic signal. The capacity for performing this measurement can be provided by a limiter 120, a frequency divider 122, a phase detector 124, and a low-pass filter 126. In operation, the limiter 120 is connected to the outputted terminal of the receiver 96, and substantially limits the amplitude of the receiver output signal so as to convert the essentially sinusoidal waveform outputted by the receiver 96 to a substantially rectangular waveform indicated at 128. The divider 122 is connected to the output signal of the counter 110 to provide a square wave signal which is phase locked to the sinusoidal signal outputted by the look-up table 112. By way of example in the construction of the divider 122, the divider 122 may comprise a counter responsive to occurrences of the least-significant bit of the count outputted by the counter 110. Alternatively, the divider 122 may be fabricated as a read-only memory, or look-up table, outputting a square wave signal in response to addressing by the count of the counter 110. The counter of the divider 122 is reset to zero by a zero count of the counter 110, thereby to maintain synchronism between the waveform outputted by the divider 122 and the sinusoidal signal transmitted by the source 90. An output waveform 130 of the divider 122 has substantially the same shape as the waveform 128, but leads the waveform 128 by the amount of phase shift which is to be measured. The signals outputted by the limiter 120 and the divider 122 are applied to the phase detector 124 which outputs an analog signal representing the difference in phase. The signal outputted by the detector 124 is smoothed by the low-pass filter 126 to provide a signal at terminal A representing the phase signature. A model phase signature provided for purposes of illustration, is shown in the graph of FIG. 11, identified by the letter A.

The signal processor 98 also can have the capacity to measure the amplitude of the received sonic signal, this capacity being provided by an analog-to-digital converter 132, a sine look-up table 134, a cosine look-up table 136, a synchronous detector 138, a digital-to-analog converter 140, and a low-pass filter 142. In operation, the converter 132 is connected to the output terminal of the receiver 96 for converting the analog signal to digital format. The look-up tables 134 and 136 are addressed by the count of the state counter 110 to output stepwise approximations to sinusoidal and cosinusoidal reference signals for use by the synchronous detector 138. The signal outputted by the converter 132 is applied to an input terminal of the synchronous detector 138. The detector 138 operates, in well-known fashion, to provide both in-phase and quadrature detection of the received signal to output a signal representing the amplitude of the received signal. The signal outputted by the detector 138 is applied to the converter 140 for conversion from digital format to analog format, and is then applied to the low-pass filter 142 to be smoothed. The signal outputted by the low-pass filter 142 at terminal B represents the amplitude signature of the received sonic signal. A model amplitude signature, provided for purposes of illustration, is shown in the graph of FIG. 11 and identified by the letter B.

According to a particularly preferred embodiment, a signature based on a combination of both amplitude and phase data may be provided by the signal processor 98. This can be accomplished by use of an encoder 144, an adder 146, a digital comparator circuit 148, a sampling circuit 150, and a low-pass filter 152. In operation, the encoder 144 is set to a value of phase by the microprocessor 84 wherein a first sample window 154 (shown in the graph of FIG. 12) is to be established. This value of phase is fed to the comparator circuit 148. A second sample window 156 (also shown in FIG. 12) is located later in time and at a phase shift of 180° relative to the location of the first sample window 154. Alternatively, the second sample window 156 can be located at a phase shift of 90° and is also controlled by the microprocessor 84. The locating of the second sample window 156 is accomplished by adding the equivalent of 180° to the phase of the first sample window 154, this addition being accomplished by use of the adder 146. In the foregoing example of a sinusoid constructed of thirty-two phase increments, the encoder 144 also outputs any one of a set of thirty-two values of phase increments. Accordingly, the addition of the adder 146 is accomplished by an addition of a count of eight or sixteen to the number outputted by the encoder 144. The output of the adder 146 is also fed to the comparator circuit 148. The count of the counter 110 is applied to an input terminal of the comparator circuit 148. The comparator circuit 148 identifies the occurrences of the phase angles of the sample windows 154 and 156 so as to strobe the sampling circuit 150 to sample the received signal outputted by the receiver 96. It should be noted here that the signal can also be measured in quadrature, that is a phase shift of 90° can be used.

Figure 12:
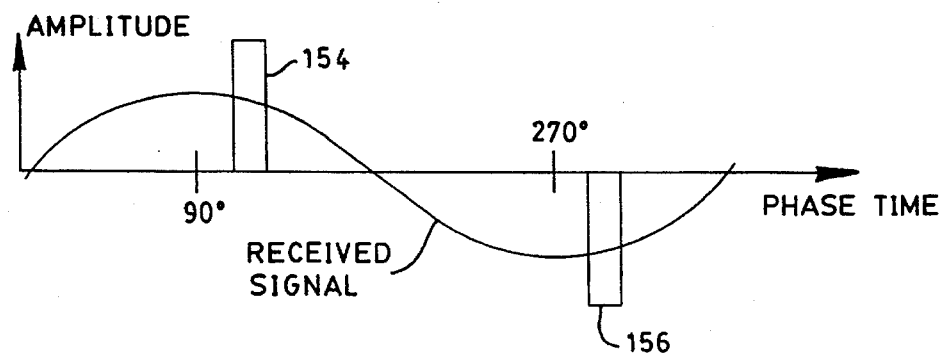
FIG. 12 is an illustrative received signal waveform.

By inspection of FIG. 12, it is noted that the two samples are of opposite sign, the sample in the sample window 154 being positive, and the sample of the sample window 156 being negative. The low pass filter 152 measures the difference between the two samples 154 and 156 thus removing any common mode signal errors. The succession of samples is integrated by the filter 152 to provide a smooth value of signal amplitude at terminal C, the signal at terminal C representing an amplitude signature based on both signal amplitude and on a relative phasing between the received signal and the succession of sampling windows 154, 156.

The effect of phase shift on the signal measurement at terminal C may be understood with reference to FIG. 12 wherein a positioning of the windows 154 and 156 respectively at 90° and 270° would maximize signal amplitude. However, as shown in the graph, the windows 154 and 156 have been applied at higher angles of phase shift, approximately 120° and 300°. Thus, the signal amplitude obtained with the phasing of FIG. 12 is less than maximum. FIG. 11 shows the relationship of received sonic signal amplitude and phase as a function of proximity of the liquid level in the reservoir 28 (FIG. 1) relative to the tip orifice 58. It has been found experimentally that, when the liquid level is distant from the orifice 58, sonic energy can exit the tip 24. However, when the tip 24 is brought into contact with the liquid 26, the orifice 58 is closed, thereby preventing escape of the sonic energy. As a result, the intensity of the sound within the tip cavity 52 and the holder chamber 62 changes. This is shown in the amplitude graph of FIG. 11. It may also be observed, by use of an oscilloscope connected at the display 118 (FIG. 7) that upon approach of the tip 24 to the liquid 26, there is a rapid increase in phase immediately before contact between the tip 24 and the liquid 26. On the display 118, this is shown as a rapid shifting of the received waveform to the right by an amount of approximately 90°. Accordingly, in FIG. 12, the locations of the windows 154 and 156 have been adjusted to the right by an amount of approximately 30°. Thus, as the tip 24 approaches the liquid 26, there is a decrease in received signal amplitude due to both the amplitude and the phase signatures of FIG. 11 allowing the received signal at terminal C to go negative upon contact with the liquid. This is useful for making a more precise determination of the location of the level of the liquid 26 relative to the tip orifice 58. As noted previously, whether the received signal increases in phase and/or intensity as the pipette tip approaches the surface of interest is dependent upon the configuration of the pipette and the frequency of the sound generated.

Figure 8:
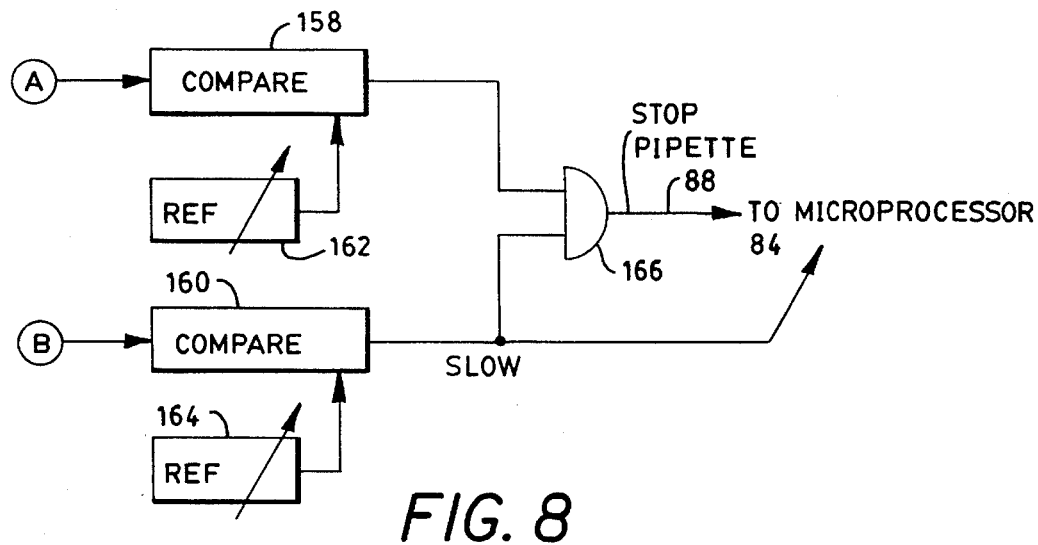
FIGS. 8, 9, and 10 show additional circuitry for inclusion in a signal processor of the liquid dispensing apparatus.

FIG. 8 shows further circuitry of the signal processor 98 which may be employed for combining data of the signatures at terminals A and B to provide an output signal on line 88 (FIG. 1) for signaling the microprocessor 84 to stop advancement of the pipette. The circuitry of FIG. 8 includes two comparators 158 and 160, two sources 162 and 164 of reference signal and an AND gate 166. In operation, the reference source 162 is adjusted to produce a reference signal having a value slightly less than the maximum value of the phase signal (Graph A) of FIG. 11. Similarly, the source 164 is adjusted to provide a value of reference signal slightly less than the maximum value of the amplitude signal (Graph B) of FIG. 11. The signal of terminal A is compared with the reference of the source 162 by the comparator 158 to output a signal to a first input terminal of the AND gate 166. Similarly, the comparator 160 compares the amplitude of the signal at terminal B with the reference signal of the source 164 to output a signal to a second input terminal of the AND gate 166. As may be seen by reference to FIG. 11, the amplitude AND gate 166 of the terminal B signal begins to change to a smaller value before the terminal B signal begins its increase upon approach of the pipette tip to the level of the liquid in the reservoir 28 (FIG. 1). Thus, the amplitude of the terminal B signal gives an earlier warning, and may serve as an indication to the microprocessor 84 to slow down the movement of the pipette 22 as it advances towards the liquid 26. Then, the phase signal of terminal A reaches its elevated value to indicate contact between the pipette tip 24 and the liquid 26. Upon the presence concurrently of the output signals of both comparators 158 and 160, the AND gate 166 outputs a signal on line 88 to stop advancement of the pipette. However, if desired, the signal outputted by the comparator 160 may be applied also to the microprocessor 84 as a slow-down signal for slowing movements of the pipette 22.

The signature (phase and amplitude) can also be generated by sweeping the frequencies of the sound and generating the signals:

1. $f(\phi)-f(\phi+180°)$ and
2. $f(\phi)-f(\phi+90°)$ (quadrature)

and measuring the outputs at terminal C and determining the phase and amplitude at each frequency.

Those skilled in the art will appreciate that a Bode plot can be generated when both the 90° and 180° signal samples are obtained. By generating such a plot for various conditions, the optimum frequency and sampling phase for each of the various functions which can be performed can be determined. Of course, it will be apparent that one frequency can be used for all applications where appropriate or different frequencies can be used for different functions as desired.

Figure 9:
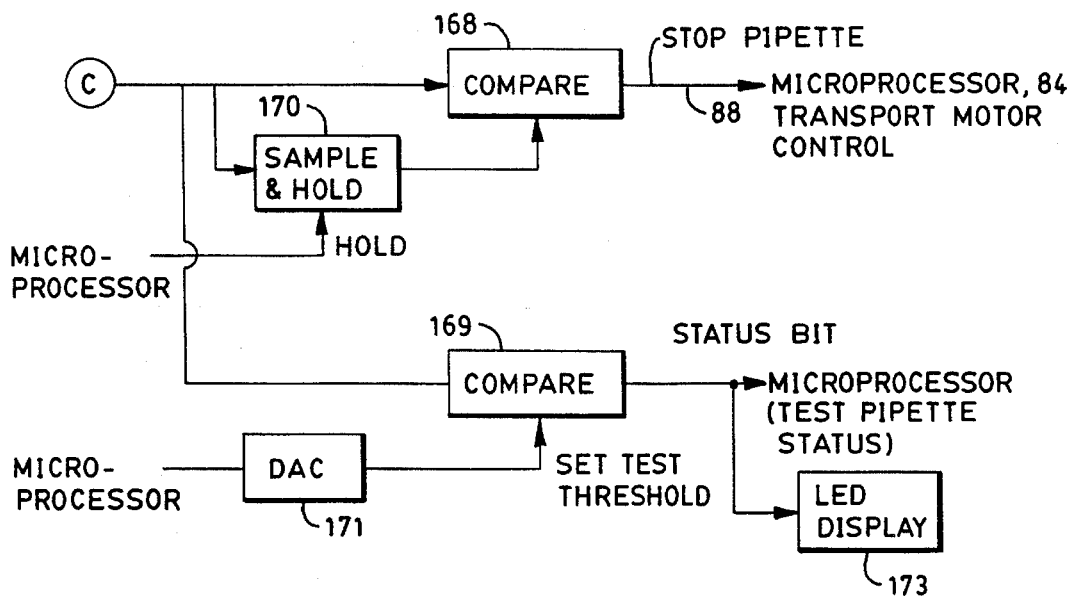

FIG. 9 shows additional circuitry which may be employed in the signal processor 98 for analysis of the signature at terminal C representing the combined effects of both amplitude and phase shift in the received sonic signal. The circuitry of FIG. 9 comprises comparator 168 and a sample-and-hold circuit 170 of the incoming signal. The sample-and-hold output 170 is used to acquire a reference to the comparator 168 prior to movement of the pipette assembly. This is applied to the comparator 168 to provide for comparison of the initial signal at terminal C with that of the present state. When the signal outputted by terminal C transitions from the reference generated by the sample-and-hold 170, the comparator 168 outputs a signal on line 88 to signal the microprocessor 84 to stop further advancement of the pipette. Further circuitry comprising a comparator 169 and a microprocessor-controlled DAC (digital to analog converter) 171 provides a programmable reference to the comparator 169. Adjusting the DAC 171 allows the microprocessor to test the signal output C to detect other pipette modes/configurations. An LED display 173 provides status information to the operator.

It should be noted here that when reference is made to the microprocessor 84 it is intended to include any number of embedded single chip controllers (not shown), each of which is typically utilized to control the operation of a stepper motor for driving various assemblies such as the pipette transport 44, the pipette piston 74 etc., within the clinical analyzer.

Figure 10:
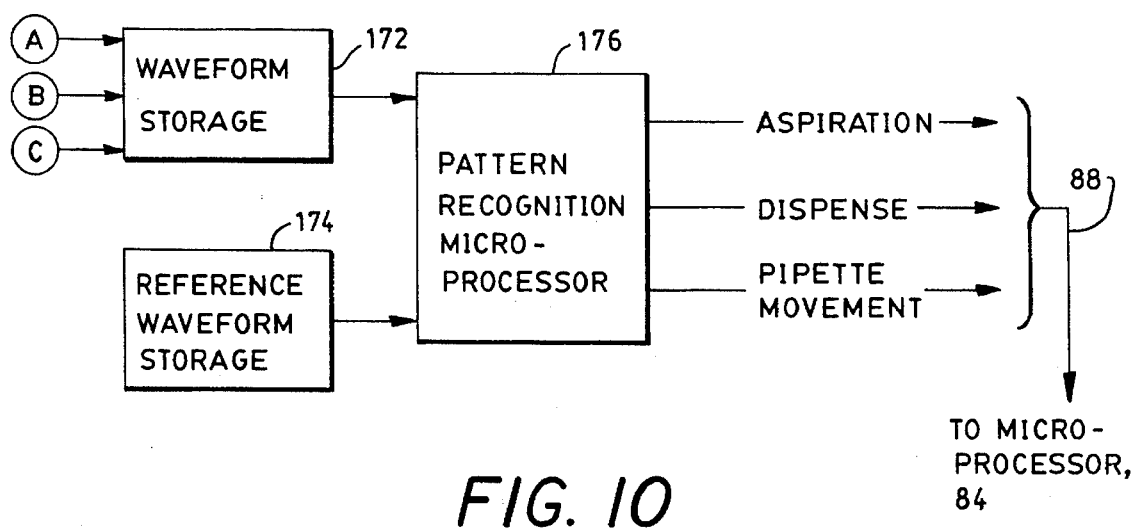

FIG. 10 shows a more general situation in which the signal processor 98 is provided with two memories 172 and 174, and a pattern recognition microprocessor 176. The memory 172 stores a history, or waveform, of the signal signature of each of the terminals A, B, and C at various frequencies of interest to distinguish between various modes of operation. Corresponding waveforms are stored in the memory 174. The microprocessor 176 then compares the data waveforms of the memory 172 with the reference waveforms of the memory 174 to determine the relative position of the level of the liquid 26 (FIG. 1) with respect to the orifice 58 of the pipette tip 24. This information is then transmitted via line 88 to the microprocessor 84 to assist in the positioning of the pipette 22. In the same fashion, further reference waveforms can be stored in the memory 174 providing data of the received sound signal as a function of a rising level of liquid within the tubular passage 56 of the tip 24, and even further rising of the liquid into the tip cavity 52. The additional reference waveforms may be obtained for sonic signals at the aforementioned relatively low frequency of 500 Hz, or at higher sonic frequencies such as 2500 Hz, or even 5000 Hz. At the higher frequencies, resonances within the tip cavity 52 and the holder chamber 62 introduce more complex shapes to the waveforms which are advantageous for precise measurements of the liquid level within the pipette tip 24. This information is transferred to the microprocessor 84 to indicate when aspiration of liquid and/or the dispensing of liquid is to be terminated to provide for a desired amount of liquid reagent to be aspirated or dispensed.

Figure 13:
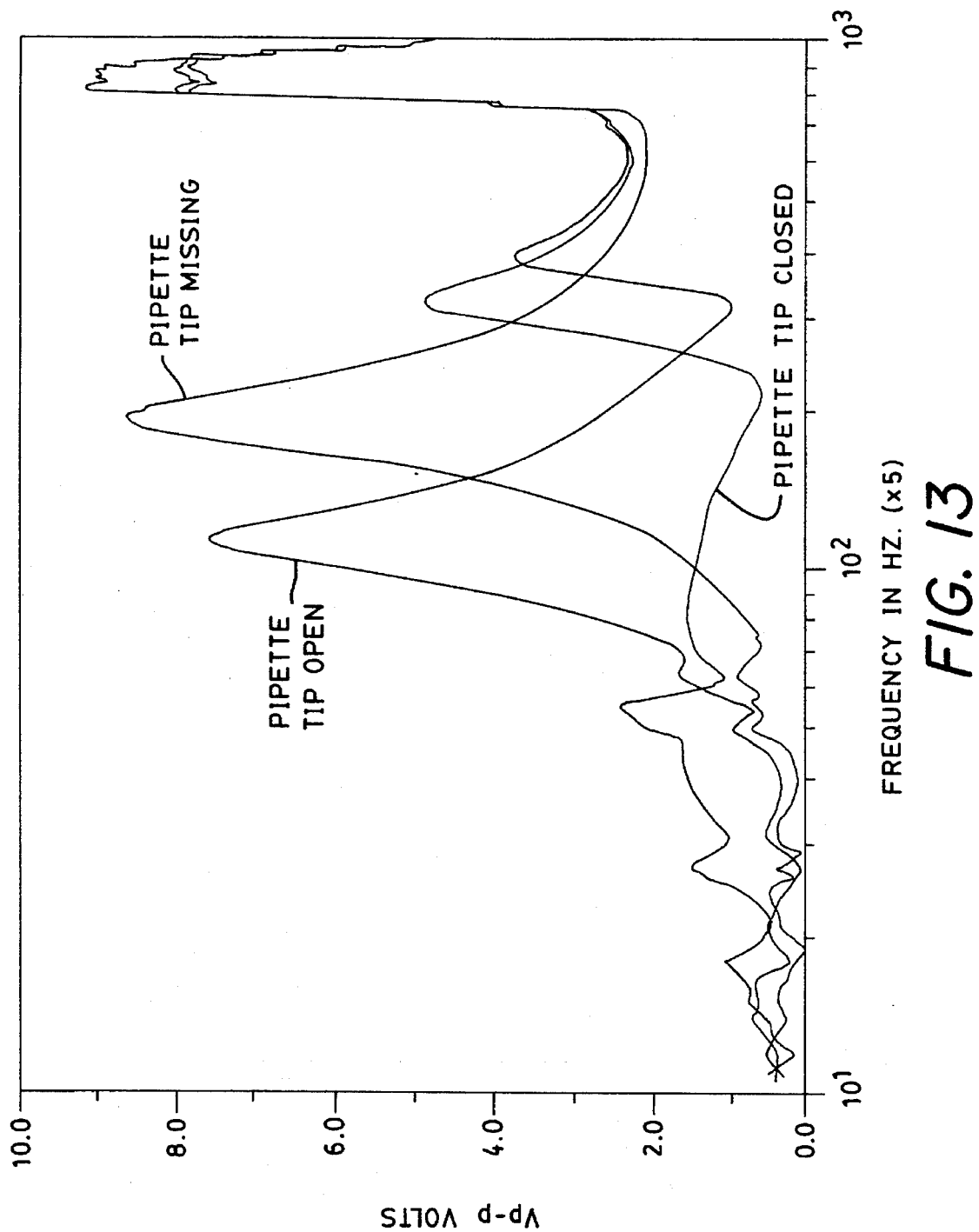
FIG. 13 is an amplitude vs frequency plot obtained for various configurations of the liquid dispense system of FIG. 1.
Figure 14:
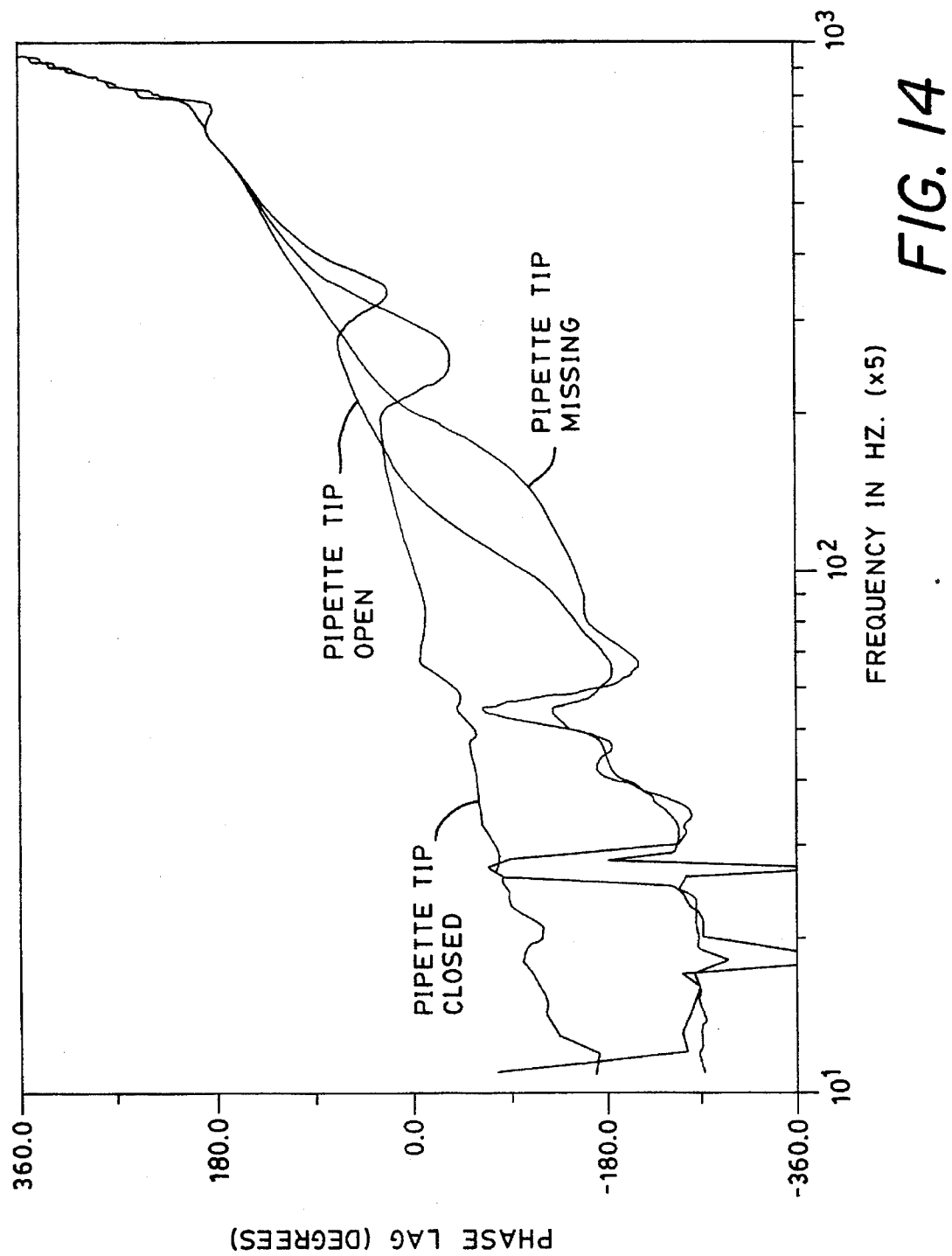
FIG. 14 is a phase vs frequency plot obtained for the same configurations of the liquid dispense system of FIG. 1.

FIGS. 13 and 14 show Bode plots obtained according to the liquid dispense system of the invention for three different pipette modes/configurations, with FIG. 13 showing the amplitude vs frequency and FIG. 14 showing the phase (lag) vs frequency. These plots show the amplitude and phase (lag) vs frequency for: a pipette which does not have any pipette tip installed ("pipette tip missing"); a pipette with a disposable pipette tip installed but not occluded ("pipette tip open"); and a pipette with a pipette tip installed and occluded ("pipette tip closed"). These Figures show the effects of both the acoustic response as well as the electronic signal filtering at both the sound generator and sound detector.

Upon examination of the voltage amplitude signature (FIG. 13) it can be seen that the "pipette tip open" configuration yields a peak voltage amplitude at approximately 500 Hz with a phase lag of approximately −90° at this frequency as determined by the corresponding phase lag signature (FIG. 14) while the "pipette tip closed" configuration has a 0° phase lag at this frequency. It can also be seen that the "pipette tip missing" configuration signature has approximately a −145° phase lag and a minimal amplitude value at 500 Hz.

Obtaining the C combination signature output with a positive sample 150 (FIG. 7) at −90° (encoder 144) and with a negative sample 150 at 90° (adder 146) allows a distinction between the "pipette tip open" configuration (with a high signal output) and either a "pipette tip closed" mode or a "pipette tip missing" mode, each yielding a lower output. It can also be seen that operation at other frequencies may distinguish between other modes of operation.

Thus, it can be seen from the foregoing that according to the invention, the signature of the pipette with a pipette tip attached is analyzed and compared with that of a pipette tip touching the liquid. An optimum operating frequency can then be chosen to maximize the demodulated signal transition. A trip point threshold can also be chosen to which the signal is to be compared. The information is stored in the memory of the microprocessor. The level sensing function is initialized with the selected frequency, phase and threshold trip point. The microprocessor may examine the status by either examining the output of the comparator or the demodulated voltage by means of an analog to digital converter. Prior to advancing the pipette toward the surface to be detected, the liquid dispense system can latch the present demodulated analog level in a sample and hold amplifier. This level can be used to generate the threshold for the comparator which in turn can be used to control directly the vertical motion control of the pipette. The system can further detect whether a desired level of liquid has been aspirated into the pipette tip, by testing the signal processor 98 outputs.

In another preferred embodiment of the invention the liquid dispense system can be utilized to determine whether a pipette tip has been picked up by the pipette head. The signature of the acoustic signal obtained with a pipette tip attached is compared with that when a tip is not present. An optimum phase, frequency and threshold trip point can be determined and the microprocessor initialized to these conditions. Examination of the output of the comparator will indicate whether a tip is present on the pipette head.

The liquid dispense system of the invention can also be utilized to calibrate the pipette position in the automated chemical analyzers. In order for the assays to be conducted properly in such automated analyzers, it is necessary that the pipette head assembly and, when present, the disposable tip secured thereto, be positioned accurately for aspiration of liquid and for dispensing of the liquid. Aspiration of a small amount of liquid from a small container requires accurate positioning of the pipette tip to ensure that no air bubbles are aspirated along with the liquid because of the resulting poor volumetric measurement. Further, the sample cup carriers and the pipette tip carriers are typically formed as molded plastic parts and their dimensions may vary slightly from one another. Similarly, the assay modules typically have a molded plastic housing the dimensions of which may vary slightly from one module to another. Also, in order to obtain an accurately dispensed sample of liquid within the well of an assay module it is necessary that the pipette tip orifice be at a precisely controlled location above a central portion of the well of the module.

The requirements of precision and accuracy in the positioning of the pipette can be accomplished by properly calibrating the liquid dispense system to account for any minor variations which may be present in the attitude of a sample tray and any minor deviations from the expected position of the various components of the instrument. Thus, in automated analyzers, it is desirable to have the capability to calibrate the liquid dispense system to minimize errors in the assay results which would otherwise occur because of the reasons previously discussed.

Prior copending commonly assigned patent application Ser. No. 654,877, now U.S. Pat. No. 5,318,868, filed Feb. 13, 1991, discloses a method for calibrating the pipette position in an automated analyzer which comprises aligning a pipette stem with targets located at various locations within the analyzer. For example, two targets can be located on a tray carrying a plurality of reservoirs for holding liquids and a target can be located on a dummy assay module which can be arranged on the conveyor within the instrument which carries the test modules during the assay procedure. In operation of the calibration method there is used an indicator having a spring-loaded tab in conjunction with a pipette stem modified by the inclusion of a circumferential slot for receiving the spring-loaded tab. The stem is inserted into the indicator and locked therein with limited sliding being provided by movement of the tab within the confines of the slot. Alignment marks are provided on both the pipette stem and the indicator to permit visual alignment of the stem relative to a target upon contact of the indication with the target. The height of the indicator along with the displacement of the pipette stem from a reference position is stored in the microprocessor.

The acoustic signal based liquid dispense system of the invention can be used in the calibration of the pipette position. The indicator device described above or a known reference pipette tip may be used for the calibration. As described previously, optimum operating parameters are determined based on the signature analysis of the acoustic signals and stored in the microprocessor. The microprocessor then is utilized to control the horizontal and vertical movement of the pipette. The comparator output can be tested to determine whether the indicator or the reference pipette tip has made contact with a desired target surface. The position of such target surface is then stored in the microprocessor and used to detect the vertical location of a tray carrying liquid containers or a tray carrying pipette tips or the surface of an assay module. An aperture in a surface, such as the liquid ingress aperture in an assay module, could also be used in the calibration technique.

The volume of liquid which has been aspirated into a pipette tip can be detected according to the invention. Higher frequency resonances, e.g., above about 1000 Hz, will be dependent upon the length of the internal air column in the pipette which in turn is affected by the level of the liquid in the pipette tip. A range of frequencies may be scanned to accurately detect that frequency which returns the greatest response. Based upon the detected frequency and the results of the signature analysis, the volume of liquid in the pipette tip may be found.

The liquid dispense system of the invention may also be utilized to determine the approach of a pipette tip to a surface. The signature of the acoustic signal obtained from an open pipette tip varies greatly from that obtained from the tip as the air opening is occluded. The pipette tip can be stopped prior to actual contact with a surface where the vertical motion is advanced with fine resolution and sufficient time is allowed for signal processing. In this instance, the actual distance of the pipette tip orifice should present a smaller cross-sectional air conduit than does the internal diameter of the pipette tip. In other words, the air conduit formed between the pipette tip and the surface is smaller than the air conduit formed in the opening of the tip.

Although the invention has been described with respect to specific preferred embodiments it is not intended to be limited thereto but rather those skilled in the art will recognize that variations and modifications may be made therein which are within the spirit of the invention and the scope of the appended claims.

What is claimed is:

1. Apparatus for aspirating and/or dispensing liquid through the use of a disposable pipette tip of the type having a rearwardly extending cavity for receiving liquid through a channel which connects the cavity to the forward end of the tip, said apparatus comprising:

a selectively moveable holder adapted to temporarily engage said pipette tip, said holder having a central chamber which communicates with the cavity of the pipette tip, which is engaged by said holder and means for creating a vacuum within the combined space defined by said central chamber and said pipette tip cavity when the forward end of said pipette tip is restricted or closed off when in proximity to a surface, means for selectively introducing an initial acoustic signal into said central chamber such that said initial acoustic signal generates an acoustic return signal at a predetermined location within said central chamber, said acoustic return signal having a characteristic signature which varies in phase and/or amplitude in accordance with the presence or absence of said pipette tip on said holder, the proximity of said holder and pipette tip to a surface, and/or the presence and amount of liquid in said pipette tip channel and cavity;

means, located at said predetermined location within said central chamber, for detecting said acoustic return signal;

means for analyzing said acoustic return signal for the properties of said characteristic signature of said acoustic return signal, including phase and/or amplitude of said characteristic signature, and providing an output response which indicates the presence or absence of said pipette tip, the proximity of said pipette tip to the surface, and/or the amount of liquid present in said pipette tip engaged by said holder;

transport means for moving said holder on a path of travel toward and away from the surface; and said means for analyzing said acoustic return signal being operationally engaged to said transport means to stop movement of the pipette tip toward the surface prior to contact of the pipette tip with the surface.

2. The apparatus as defined in claim 1 wherein said acoustic signal introducing means and said acoustic return signal detecting means are located diametrically opposite each other.

3. A method for providing information relating to a pipette in a liquid aspirating and/or dispensing system wherein said system includes apparatus comprising a selectively moveable pipette tip holder adapted to temporarily engage a disposable pipette tip having a rearwardly extending cavity for receiving liquid through a channel which connects said cavity to the forward end of said tip, said pipette tip holder having a central chamber which communicates with the cavity of the pipette tip, which is engaged by said pipette tip holder and means for creating a vacuum within the combined space defined by said central chamber and said pipette tip cavity when the forward end of said pipette tip is restricted or closed off when in proximity to a surface, the method comprising the steps of moving said holder on a path of travel toward the surface;

selectively introducing an initial acoustic signal into said central chamber such that said initial acoustic signal generates an acoustic return signal at a predetermined location within said central chamber, said acoustic return signal having a characteristic signature which varies in phase and/or amplitude in accordance with the presence or absence of said pipette tip on said holder, the proximity of said holder and pipette tip to the surface and/or the presence and amount of liquid in said pipette tip channel and cavity;

detecting said acoustic return signal at a predetermined location within said central chamber;

analyzing said acoustic return signal for the properties of said characteristic signature of said acoustic return signal including phase and/or amplitude of said characteristic signature;

providing an output response which indicates the presence or absence of said pipette tip, proximity of said pipette tip to said surface and/or the amount of liquid present in the pipette tip; and stopping further movement toward the surface prior to contact of the pipette tip with the surface.

4. A method for detecting the position of a pipette tip relative to the surface of a liquid in a liquid aspirating and/or dispensing system wherein said system includes apparatus comprising a selectively moveable pipette tip holder adapted to temporarily engage a disposable pipette tip having a rearwardly extending cavity for receiving liquid through a channel which connects said cavity to the forward end of said tip, said pipette tip holder having a central chamber which communicates with the cavity of the pipette tip, which is engaged by said pipette tip holder and means for creating a vacuum within the combined space defined by said central chamber and said pipette tip cavity when the forward end of said pipette tip is restricted or closed off when in proximity to a surface, the method comprising the steps of transporting said pipette on a path of travel toward a liquid residing in a container;

selectively introducing an initial acoustic signal into said central chamber such that said initial acoustic signal generates an acoustic return signal at a predetermined location within said central chamber, said acoustic return signal having a characteristic signature which varies in phase and/or amplitude in accordance with the proximity of said holder and pipette tip to the surface of said liquid;

detecting said acoustic return signal at a predetermined location within said central chamber;

analyzing said acoustic return signal for the properties of said characteristic signal of said acoustic return signal including phase and/or amplitude of said characteristic signal;

providing an output response which indicates when said pipette tip is in proximity to the surface of said liquid prior to the pipette tip making contact with the surface;

stopping further transport of said pipette toward the surface when said output response indicates that said pipette tip is in proximity to the surface of said liquid prior to penetrating the surface of said liquid;

reinitiating transport of said pipette on the path of travel toward said liquid; and stopping further transport of said pipette when said pipette tip has penetrated a desired distance into said liquid.

5. The method as defined in claim 4 and further including the steps of aspirating a desired volume of said liquid into said pipette tip and retracting said pipette tip from said liquid.

6. The apparatus as defined in claim 1 wherein the means for analyzing the acoustic return signal analyzes both phase and amplitude.

7. The apparatus as defined in claim 1 wherein the means for selectively introducing the initial acoustic signal into said central chamber introduces the initial acoustic signal within a frequency range from about 400 to 600 Hz.

8. The apparatus as defined in claim 1 wherein the means for analyzing the acoustic return signal is operationally engaged to the transport means to stop movement of the pipette tip toward the surface such that a first air conduit formed by a distance between the pipette tip and the surface is less than a second air conduit formed by an internal opening of the pipette tip.

9. The apparatus as defined in claim 1 wherein the means for creating a vacuum within the combined space defined by said central chamber and said pipette tip cavity is a piston means moveable within said central chamber.

10. The method as defined in claim 3 wherein the step analyzing the acoustic return signal analyzes both phase and amplitude.

11. The method as defined in claim 3 wherein the step of selectively introducing the initial acoustic signal into said central chamber introduces the initial acoustic signal within a frequency range from about 400 to 600 Hz.

12. The method as defined in claim 3 wherein the step of stopping further movement toward the surface prior to contact of the pipette tip with a surface occurs when the pipette tip is at a distance from the surface such that a first air conduit formed by the distance between the pipette tip and the surface is less than a second air conduit formed by an internal opening of the pipette tip.

13. The method as defined in claim 3 wherein the means for creating a vacuum within the combined space defined by said central chamber and said pipette tip cavity is a piston means moveable within said central chamber.

14. The method as defined in claim 9 wherein the step analyzing the acoustic return signal analyzes both phase and amplitude.

15. The method as defined in claim 9 wherein the step of selectively introducing the initial acoustic signal into said central chamber introduces the initial acoustic signal within a frequency range from about 400 to 600 Hz.

16. The method as defined in claim 4 wherein the step of stopping further movement toward the surface prior to contact of the pipette tip with a surface occurs when the pipette tip is at a distance from the surface such that a first air conduit formed by the distance between the pipette tip and the surface is less than a second air conduit formed by an internal opening of the pipette tip.

17. The method as defined in claim 4 further including the step of providing an output response which indicates when said pipette tip has entered said liquid.

18. The method as defined in claim 4 wherein the means for creating a vacuum within the combined space defined by said central chamber and said pipette tip cavity is a piston means moveable within said central chamber.

* * * * *